United States Patent
Edwards

(10) Patent No.: US 8,019,412 B2
(45) Date of Patent: Sep. 13, 2011

(54) APPARATUS FOR FACILITATING TRANSDERMAL DELIVERY OF THERAPEUTIC SUBSTANCES AND METHOD OF TRANSDERMALLY DELIVERING THERAPEUTIC SUBSTANCES

(75) Inventor: Jeffrey D. Edwards, Claremont (AU)

(73) Assignee: International Scientific Pty Ltd., Leederville, Western Australia (AU)

( * ) Notice: Subject to any disclaimer, the term of this patent is extended or adjusted under 35 U.S.C. 154(b) by 615 days.

(21) Appl. No.: 10/595,964

(22) PCT Filed: Nov. 18, 2004

(86) PCT No.: PCT/AU2004/001599
§ 371 (c)(1),
(2), (4) Date: May 9, 2007

(87) PCT Pub. No.: WO2005/049135
PCT Pub. Date: Jun. 2, 2005

(65) Prior Publication Data
US 2007/0293810 A1 Dec. 20, 2007

(30) Foreign Application Priority Data
Nov. 21, 2003 (AU) ............................... 2003906428

(51) Int. Cl.
*A61N 1/30* (2006.01)
*A61K 9/22* (2006.01)
(52) U.S. Cl. ...................... 604/20; 604/890.1
(58) Field of Classification Search .............. 604/20, 604/153, 891.1
See application file for complete search history.

(56) References Cited

U.S. PATENT DOCUMENTS

| 4,315,503 | A | 2/1982 | Ryaby et al. |
| 4,428,366 | A | 1/1984 | Findl et al. |
| 5,190,761 | A | 3/1993 | Liburdy |
| 5,314,400 | A | 5/1994 | Tsyb et al. |
| 5,669,868 | A | 9/1997 | Markoll |
| 6,443,883 | B1 | 9/2002 | Ostrow et al. |
| 6,564,093 | B1 | 5/2003 | Ostrow et al. |
| 6,574,504 | B1 | 6/2003 | Mazaury et al. |
| 2002/0147424 | A1 | 10/2002 | Ostrow et al. |
| 2003/0073949 | A1 | 4/2003 | Giammarusti |

FOREIGN PATENT DOCUMENTS

| FR | 2781162 | | 1/2000 |
| GB | 2307862 | A | 6/1999 |
| WO | 9615829 | A2 | 5/1996 |
| WO | 0003762 | A1 | 1/2000 |

*Primary Examiner* — Nicholas D Lucchesi
*Assistant Examiner* — Victoria P Campbell
(74) *Attorney, Agent, or Firm* — Davis Wright Tremaine LLP; George C. Rondeau, Jr.

(57) ABSTRACT

An apparatus (40) is disclosed for facilitating transdermal delivery of therapeutic substances. The apparatus (40) comprises means (44) for producing an electromagnetic field, control means (26, 34) arranged to control said field producing means to alternately produce active and substantially inactive electromagnetic field portions. Each active electromagnetic field portion includes an electromagnetic field packet having a plurality of successive electromagnetic field pulses, and each substantially inactive electromagnetic field portion includes no electromagnetic field pulses. During use, when the electromagnetic field is incident on a patient, dermal permeability is increased. A corresponding method is also disclosed.

29 Claims, 3 Drawing Sheets

APPARATUS FOR FACILITATING TRANSDERMAL DELIVERY OF THERAPEUTIC SUBSTANCES AND METHOD OF TRANSDERMALLY DELIVERING THERAPEUTIC SUBSTANCES

FIELD OF THE INVENTION

The present invention relates to an apparatus for facilitating transdermal delivery of therapeutic substances and to a method of transdermally delivering therapeutic substances.

BACKGROUND OF THE INVENTION

The use of therapeutic substances to treat and/or prevent disease, injury or disability is a cornerstone of modern human and animal related medicine.

In order for such therapeutic substances to have useful effect to a desired treatment area, the substances must be physically and/or chemically available to the treatment area, and must be available in a sufficient concentration to exert a beneficial biological effect.

As an alternative to conventional methods of delivery of therapeutic substances, transdermal delivery techniques have been developed so that a degree of site specificity is obtained and a desired concentration of therapeutic substance is achieved which is unaltered by digestion or blood chemistry. Transdermal delivery techniques also offer the possibility of high user compliance, ease of management, low toxicity and high cost effectiveness.

However, mammalian skin poses a significant barrier to entry for many therapeutic substances because the lipid bilayer of the stratum corneum skin layer generally only allows very small neutrally charged particles of the order of 1 nm to pass through. As such, transdermal delivery of many ions, drugs, macro molecules, DNA fragments, genes and therapeutic substances is problematic.

In one transdermal technique referred to as iontophoresis, an electrical energy gradient is used to charge a target molecule and an electrical voltage is employed to accelerate the charged target molecule towards a cell membrane adjacent the target area, the energy of the target molecule being sufficient to cause the target molecule to pass through the cell membrane.

However, due to the relatively high energy levels employed, significant residual cellular damage occurs to the skin which can manifest as localised burns, skin irritation and cellular fatigue. In addition, critical ionic structures of the target molecule can be inadvertently changed by the process.

A further transdermal delivery technique is referred to as electroporation. With this technique, successive pulses of 1 ms to 10 ms duration of the order of 100 to 200 volts are directly applied to a target skin area using probes.

However, as with the iontophoresis technique, since relatively high energy levels are used, significant cellular damage occurs. In addition, in view of the high voltages employed, electroporation is unsuitable to use in vivo and to date has been used only in vitro.

The barrier effect of the stratum corneum arises as a result of the intercellular lipid matrix which comprises long chain ceramides, free fatty acids, cholesterol and other lipids. The lipids are arranged into bilayers having hydrocarbon chains aligned to form an oily bilayer core and electrically charged or polar outwardly facing head groups. This produces a highly selective filter-like structure. In contrast to phospholipid bilayer membranes found elsewhere in the body, the composition of the stratum corneum lipid bilayers is a much more rigid and ordered structure. As a consequence, the barrier to penetration of the stratum corneum by therapeutic substances is much greater compared to the corresponding barriers to penetration produced by other body membranes.

Therapeutic substance delivery techniques such as iontophoresis and electroporation rely on introducing sufficient energy to the stratum corneum to break up the inherent structure of the lipid bilayer, which disrupts the hydrophilic-hydrophobic orientation of the bilayer and creates regions of random orientation through which some substances may be introduced. Disruption of the dermal barrier effect in this way is unpredictable and provides little control over the rate of drug delivery.

In the claims of this application and in the description of the invention, except where the context requires otherwise due to express language or necessary implication, the words "comprise" or variations such as "comprises" or "comprising" are used in an inclusive sense, i.e. to specify the presence of the stated features but not to preclude the presence or addition of further features in various embodiments of the invention.

SUMMARY OF THE INVENTION

In accordance with an aspect of the present invention, there is provided an apparatus for facilitating transdermal delivery of therapeutic substances, said apparatus comprising:
  means for producing an electromagnetic field;
  control means arranged to control said field producing means to alternately produce active and substantially inactive electromagnetic field portions, each said active electromagnetic field portion including an electromagnetic field packet having a plurality of successive electromagnetic field pulses, and each said substantially inactive electromagnetic field portion including no electromagnetic field pulses;
  wherein during use when the electromagnetic field is incident on a patient, dermal permeability is increased.

In one arrangement, the means for producing an electromagnetic field includes a coil. The means for producing an electromagnetic field may further include a solid state switching device which may be a transistor such as a bipolar transistor connected in series with the coil.

In one arrangement, the control means is arranged to produce an energisation signal useable to control switching of the solid state switching device, the energisation signal including a repeating energisation signal packet, each energisation signal packet including a plurality of energisation signal pulses of generally rectangular configuration.

The control means may comprise a microcontroller which may be programmable by a user. The microcontroller may be programmed such that dermal permeability is increased at one or more specific times, permeability is increased for a specific period of time, and so on.

In one embodiment, the energisation signal packet repeats at a frequency of between 1 Hz and 100 Hz, more particularly between 10 Hz and 50 Hz.

In one arrangement, each energisation signal packet includes between 12 and 20 energisation signal pulses.

In one arrangement, the duration of each energisation signal pulse is between 1 µs and 1 s, more particularly between 25 µs and 100 ms.

The apparatus may take the form of a generally flat member having the means for producing an electromagnetic field and the control means embedded therein.

In one arrangement, the therapeutic substance is disposed on a surface of the apparatus. The therapeutic substance may be a drug, vaccine, ion, macromolecule, DNA fragment, gene or any other substance desired to be passed through the skin of a patient for the purpose of obtaining a beneficial effect.

In accordance with an alternative aspect of the present invention, there is provided a method of transdermally delivering therapeutic substances, said method comprising:
producing an electromagnetic field;
directing the electromagnetic field at a desired treatment area of a patient's skin; and
controlling the electromagnetic field so as to alternately produce active and substantially inactive electromagnetic field portions, each said active electromagnetic field portion including an electromagnetic field packet having a plurality of successive electromagnetic field pulses, and each said substantially inactive electromagnetic field portion including no electromagnetic field pulses.

BRIEF DESCRIPTION OF THE DRAWINGS

The present invention will now be described, by way of example only, with reference to the accompanying drawings, in which.

DESCRIPTION OF AN EMBODIMENT OF THE INVENTION

Figure 1:
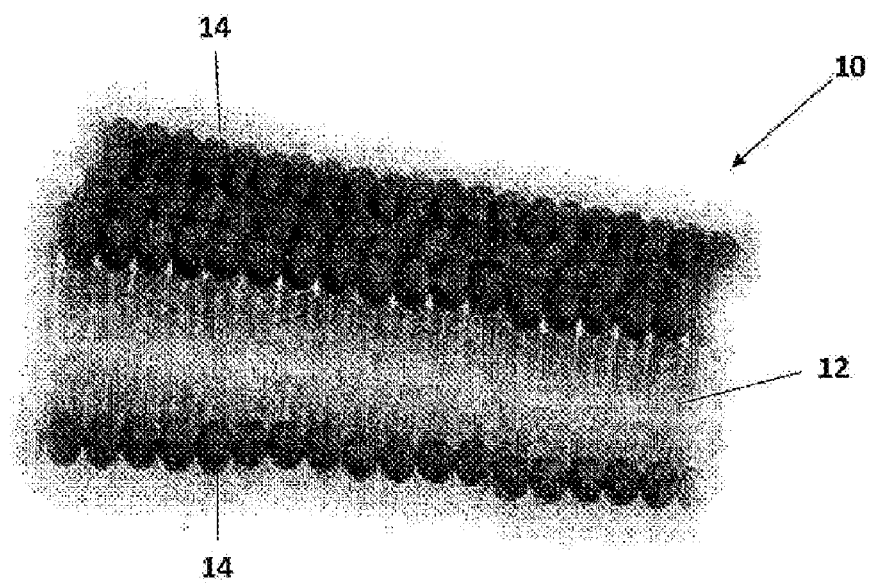
FIG. 1 is a diagrammatic perspective view of a portion of a stratum corneum prior to application of an electromagnetic field produced in accordance with an apparatus and method according to the present invention.

Referring to the drawings, in FIG. 1 a portion of a stratum corneum lipid bilayer structure 10 is shown diagrammatically, the lipid bilayer structure 10 having an oily core portion 12 formed of aligned hydrocarbon chains, and charged head portions 14.

During normal conditions, the bilayer structure 10 serves to prevent particles having a size greater than approximately 1 nm from passing through.

Figure 2:
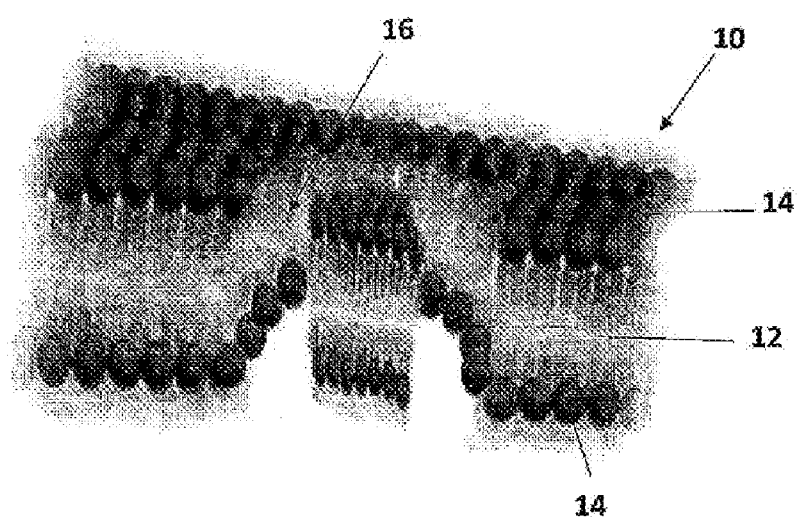
FIG. 2 is a diagrammatic perspective view of the stratum corneum shown in FIG. 1 during application of an electromagnetic field produced by an apparatus and method in accordance with an embodiment of the present invention.

The inventor of the present invention has discovered that by applying a relatively low power electromagnetic field of particular pattern to the stratum corneum, it is possible to cause at least some of the lipids to compact in such a way as to create a void or a region of low lipid population in the stratum corneum through which therapeutic substances may pass. In the present example, the electromagnetic field of predetermined pattern causes a void 16 or region of low lipid population which may be annular to be defined in the stratum corneum as shown diagrammatically in FIG. 2, the annular void 16 being temporarily present during and after application of the electromagnetic field, and the structure of the stratum corneum reverting back to the barrier structure shown in FIG. 1 at a period of time after cessation of the electromagnetic field.

Figure 3:
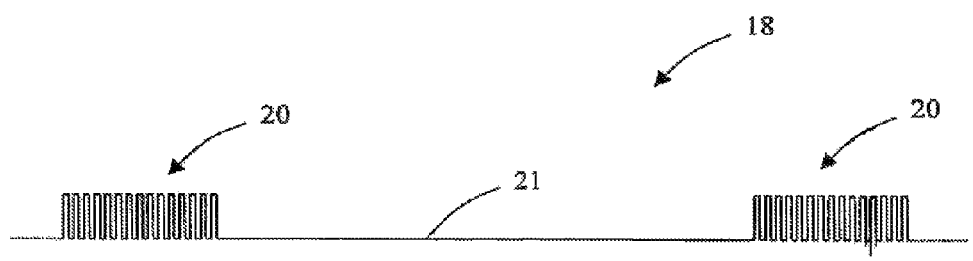
FIG. 3 is a schematic diagram of an energisation signal used to effect energisation of an electromagnetic field generation device of an apparatus in accordance with an embodiment of the present invention.

The inventor of the present invention has discovered that by applying an energisation signal 18 of the general pattern shown in FIG. 3 to control circuitry of an electromagnetic field generation device such as a coil, the desired effect of creating a temporary aperture in the stratum corneum is achieved. The energisation signal 18 has a general pattern which comprises alternating active and inactive signal portions, the active signal portions containing a plurality of voltage pulses and the inactive signal portions containing no voltage pulses.

Figure 4:
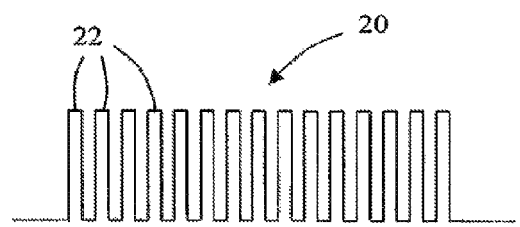
FIG. 4 is an enlarged schematic diagram of an energisation signal packet of the energisation signal shown in FIG. 3.

In particular, the energisation signal 18 may include an active signal portion in the form of an energisation signal packet 20 which repeats at a frequency of between 1 Hz and 100 Hz, more particularly between 10 Hz and 50 Hz, with each energisation signal packet including between 12 and 20 successive energisation signal pulses 22, and each successive pair of energisation signal packets 20 being separated by an inactive signal portion 21. The energisation pulses 22 are shown more particularly in an enlarged view of the energisation signal packet 20 shown in FIG. 4. The duration of each energisation pulse 22 may be of the order of 1 μs to 1 s, more particularly 25 μs to 100 ms.

In the present example, the time duration of the inactive portion 21, that is the time between successive active portions 20, is greater than the time duration of an active portion 20.

In the present example, the duration of each energisation signal pulse 22 is approximately 360 μs, the duty cycle of each of the energisation signal pulses 22 is approximately 50%, and the time duration of each inactive signal portion 21 is 15 times greater than the time duration of each active signal portion 20, although it will be understood that other variations are possible. Each energisation signal pulse 22 in the present example is of generally rectangular shape.

It will be understood that by applying energisation signal pulses 22 of generally rectangular shape to control circuitry of an electromagnetic field generation device such as a coil, active electromagnetic field portions separated by inactive electromagnetic field portions are produced, with each active electromagnetic field portion containing packets of electromagnetic field pulses produced at a spacing determined by the duration of an inactive electromagnetic field portion, and each inactive electromagnetic field portion containing no electromagnetic field pulses. In the present example, the electromagnetic field strength of the electromagnetic field signal is of the order of 3 Gauss or less.

Without wishing to be bound by theory, it is believed that permeability of the stratum corneum is enhanced by application of an electromagnetic signal of the type produced when an energisation signal of the general pattern shown in FIG. 3 is applied to control circuitry of an electromagnetic field generation device, because the plurality of electromagnetic pulses in the active field portion cause charging of portions of the bilayer structure and thereby creation of a potential difference in the structure, and the inactive field portions cause the accumulated charge to dissipate across the lipid bilayer. This causes portions of the bilayer structure to repel each other and thereby form an opening in the stratum corneum through which therapeutic substances may pass. In other words, it is believed that the electromagnetic field does not in itself have any biological effect on the stratum corneum, rather the electromagnetic field induces an electrical or ionic effect in the stratum corneum which causes gaps to occur in the stratum corneum. In view of this, it is believed that the amount of charge generated in the bilayer structure and thereby the degree of permeability is dependent in particular on the number of pulse edges of the energisation signal per unit time, the total number of pulse edges, and the packet frequency.

The inventor of the present invention has also discovered that the present transdermal delivery technique makes it possible to accurately target within 3 dimensions a desired treatment area by locating the electromagnetic field generation device (in this example a coil) above the desired treatment area, and modifying the packet frequency so as to influence the stratum corneum bilayers with little or no detectable effect in surrounding tissue.

Figure 5:
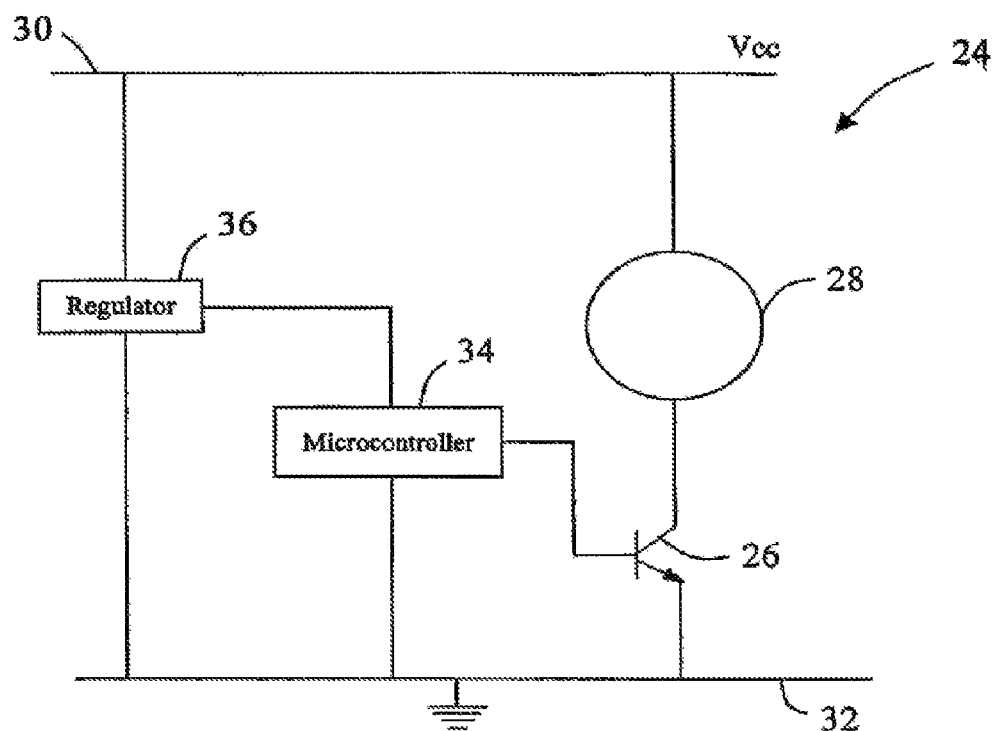
FIG. 5 is a schematic diagram illustrating circuitry of an apparatus for facilitating transdermal delivery of therapeutic substances in accordance with an embodiment of the present invention.

Referring to FIG. 5, circuitry 24 is shown for effecting generation of an electromagnetic signal having a pattern suitable for causing an aperture to be produced in a stratum corneum.

The circuitry 24 includes a solid state switching device, in this example in the form of a bipolar transistor 26, connected in series with an electromagnetic field generation device, in this example in the form of a coil 28. Transistor 26 provides a means of completing an electrical path between Vcc or supply DC voltage 30 and Ground or 0 volt DC 32 through coil 28, energizing said coil 28. Switching of transistor 26, and therefore energizing of coil 28, is controlled using control circuitry, in this example in the form of a microcontroller 34 programmed to apply a signal to the base of the transistor 26 corresponding to the general pattern of the energisation signal 18 shown in FIGS. 3 and 4. However it will be understood that other arrangements for effecting the controlled switching of transistor 26 are envisaged.

In this example, a voltage regulator 36 is also provided to produce a regulated voltage necessary for the microcontroller 34, although it will be understood that for microcontrollers or other control circuitry which do not require a regulated voltage supply, the regulator 36 may be omitted.

Figure 6:
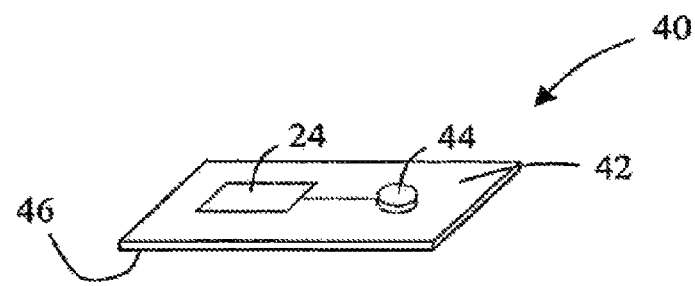
FIG. 6 is a diagrammatic perspective view of an apparatus for facilitating transdermal delivery of therapeutic substances in accordance with an embodiment of the present invention, the apparatus including the circuitry shown in FIG. 5.

As shown in FIG. 6, an apparatus 40 for facilitating transdermal delivery of therapeutic substances may take the form of a generally flat rectangular member which for example may be formed of plastics material. The apparatus 40 includes a body portion 42 having embedded circuitry 24 and an energy storage device such as a battery 44 for supplying power to the circuitry 24. However, it will be understood that other types of apparatus may be used, and that the apparatus may be mains powered.

During use, the apparatus 40 may be placed adjacent a portion of the skin through which it is desired to introduce therapeutic substances and the circuitry 24 activated so as to cause opening of an aperture in the stratum corneum adjacent the apparatus 40.

The therapeutic substance may be disposed on a surface 46 of the body portion 42, may be applied directly to the skin, or may be introduced on to the skin in any other suitable way.

In an experimental example, penetration of caffeine through excised human epidermal membranes was investigated using Franz-type diffusion cells and standard procedures. An electromagnetic field pattern was created and the penetration results compared with passive diffusion. The electromagnetic field pattern used was generated by applying an energisation signal having 12 pulses at a repeating frequency of 10 Hz to a coil Each of the pulses has a duration of approximately 360 µs. A phosphate buffered saline receptor solution was used and the amount of caffeine in the receptor solution determined by HPLC with UV detection at regular time intervals up to 6 hours post application of the electromagnetic field. In this example, the electromagnetic field pattern was applied for approximately 30 minutes.

It was observed that the caffeine flux associated with passive diffusion was of the order of 4.1 $\mu gcm^{-2}h^{-1}$. It was also observed that the caffeine flux associated with the electromagnetic field patterns of the present invention were significantly higher than the corresponding caffeine flux associated with passive diffusion, with the highest caffeine flux achieved being 19.24 $\mu gcm^{-2}h^{-1}$.

Similar experiments were carried out with electromagnetic fields generated by applying an energisation signal having 15 pulses of 360 µs duration at a repeating frequency of 20 Hz to a coil, and by applying an energisation signal having 255 pulses at a repeating frequency of 2 Hz to a coil. These experiments yielded caffeine flux values of 7.20 $\mu gcm^{-2}h^{-1}$ and 8.51 $\mu gcm^{-2}h^{-1}$, although the latter of these experiments produced an effect only after 60 minutes.

A further experiment was carried out by applying an energisation signal having a single quasi-rectangular pulse repeated at 72 Hz to a coil. This yielded no discernable change in permeability of the stratum corneum.

It will be appreciated that although the present embodiment is described in relation to common rail mode generation of an electromagnetic signal, other arrangements are possible, such as biphasic mode generation of an electromagnetic signal.

It will be appreciated that the amount of energy required to carry out the present transdermal delivery technique is approximately 1000 times less than the corresponding energy levels required for iontophoresis and electroporation transdermal delivery techniques. As a consequence, the present technique is ideally suited to implementation in compact, portable and disposable applications, in particular for outpatient and homecare use.

It will also be appreciated that since the present technique is inductive, the technique can operate through most non-conductive materials such as bandages without the requirement for physical contact with the skin.

It will also be appreciated that the present technique can not be sensed or felt by humans and, as a result, the technique is painless and has none of the undesirable side effects commonly associated with techniques such as iontophoresis and electroporation.

It will also be appreciated that the control circuitry, for example a microcontroller, may be configured so that the apparatus carries out a specific treatment plan, for example by generating an appropriate energisation signal pattern and using the energisation signal to apply one or more specific electromagnetic field patterns to a target area of a patient at specific times of for a specific time duration.

It will also be appreciated that the therapeutic substance may be a drug, vaccine, ion, macromolecule, DNA fragment, gene or any other substance desired to be passed through the skin of a patient for the purpose of obtaining a beneficial effect.

Modifications and variations as would be apparent to a skilled addressee are deemed to be within the scope of the present invention.

The invention claimed is:

1. An apparatus for facilitating transdermal delivery of therapeutic substances, said apparatus comprising:
    an electromagnetic field generating device including a coil which has electrical connectivity at both ends to allow unidirectional flow of current;
    a control device arranged to control said field generating device to alternately produce active and substantially inactive electromagnetic field portions, each said active electromagnetic field portion having a frequency of between 1 Hz and 100 Hz and comprising a plurality of generally rectangular electromagnetic field pulses wherein each electromagnetic field pulse has a duration of between 25 μs and 100 ms, each said substantially inactive electromagnetic field portion including no electromagnetic field pulses, wherein the duration of the inactive electromagnetic field portion is longer than the duration of the active electromagnetic field portion.

2. Apparatus as claimed in claim 1, wherein the electromagnetic field generating device comprises a solid state switching device.

3. Apparatus as claimed in claim 2, wherein the control device is arranged to produce an energisation signal useable to control switching of the solid state switching device to produce active and substantially inactive energisation signal portions, each active energisation signal portion including a plurality of energisation signal pulses and a substantially inactive energisation signal portion including no energisation signal pulses, and wherein the active energisation signal portion produces the active electromagnetic field portion and the inactive energisation signal portion produces the inactive electromagnetic field portion.

4. Apparatus as claimed in claim 3, wherein the active energisation signal portion repeats at a frequency of between 10 Hz and 50 Hz.

5. Apparatus as claimed in claim 3, wherein each active energisation signal portion includes between 12 and 20 energisation signal pulses.

6. Apparatus as claimed in claim 2, wherein the solid state switching device comprises a transistor.

7. Apparatus as claimed in claim 1, wherein the control device comprises a microcontroller.

8. Apparatus as claimed in claim 7, wherein the microcontroller is programmable by a user so that an electromagnetic signal corresponding to a predetermined therapeutic substance delivery plan is produced.

9. Apparatus as claimed in claim 8, wherein the microcontroller is programmed such that dermal permeability is increased at one or more specific times.

10. Apparatus as claimed in claim 8, wherein the microcontroller is programmed such that dermal permeability is increased for a specific period of time.

11. Apparatus as claimed in claim 1, wherein the apparatus comprises a substantially flat member having the electromagnetic field generating device and the control device embedded therein.

12. Apparatus as claimed in claim 1, wherein the therapeutic substance is disposed on an outwardly facing surface of the apparatus.

13. Apparatus as claimed in claim 1, wherein the therapeutic substance is a drug, vaccine, ion, macromolecule, DNA fragment or gene.

14. The apparatus of claim 1, wherein the control device includes control circuitry arranged to control said field generating device to alternately produce said active and said substantially inactive electromagnetic field portions by selectively energizing and de-energizing said field generating device while power is applied to said control circuitry.

15. The apparatus of claim 1, wherein the electromagnetic field pulses have an electromagnetic field strength of less than or equal to 3 Gauss and sufficient to facilitate transdermal delivery of therapeutic substances by increasing dermal permeability of a portion of the skin of a user of the apparatus.

16. A method of transdermally delivering therapeutic substances, said method comprising:

producing an electromagnetic field using a coil which has electrical connectivity at both ends to allow unidirectional flow of current;

directing the electromagnetic field at a desired treatment area of a patient's skin; and controlling the electromagnetic field so as to alternately produce active and substantially inactive electromagnetic field portions, each said active electromagnetic field portion having a frequency of between 1 Hz and 100 Hz and comprising a plurality of generally rectangular electromagnetic field pulses wherein each electromagnetic field pulse has a duration of between 25 μs and 100 ms, each said substantially inactive electromagnetic field portion including no electromagnetic field pulses, wherein the duration of the inactive electromagnetic field portion is longer than the duration of the active electromagnetic field portion.

17. A method as claimed in claim 16, wherein the step of controlling the electromagnetic field comprises producing an energisation signal useable to control switching of a solid state switching device to produce active and substantially inactive energisation signal portions, each energisation signal portion including a plurality of energisation signal pulses and a substantially inactive energisation signal portion including no energisation signal pulses and wherein the active energisation signal portion produces the active electromagnetic field portion and the inactive energisation signal portion produces the inactive electromagnetic field portion.

18. A method as claimed in claim 17, wherein the solid state switching device comprises a transistor.

19. A method as claimed in claim 17, wherein each active energisation signal portion includes between 12 and 20 energisation signal pulses.

20. A method as claimed in claim 16, wherein the control means comprises a microcontroller.

21. A method as claimed in claim 20, further comprising the step of programming the microcontroller so that during use an electromagnetic signal corresponding to a predetermined therapeutic substance delivery plan is produced.

22. A method as claimed in claim 21, further comprising the step of programming the microcontroller such that dermal permeability is increased at one or more specific times.

23. A method as claimed in claim 21, further comprising the step of programming the microcontroller such that dermal permeability is increased for a specific period of time.

24. A method as claimed in claim 16, wherein the active energisation signal portion repeats at a frequency of between 10 Hz and 50 Hz.

25. A method as claimed in claim 16, wherein the therapeutic substance is a drug, vaccine, ion, macromolecule, DNA fragment or gene.

26. The method of claim 16, wherein the electromagnetic field pulses have an electromagnetic field strength of less than or equal to 3 Gauss and sufficient to facilitate transdermal delivery of therapeutic substances by increasing dermal permeability of the desired treatment area of the patient's skin.

27. An apparatus for facilitating transdermal delivery of therapeutic substances, said apparatus comprising:

an electromagnetic field generating device including a solid state switching device coupled to a coil which has electrical connectivity at both ends to allow unidirectional flow of current, the solid state switching device being operative to energize the coil with direct current to selectively produce an electromagnetic field;

a control device coupled to the solid state switching device to control said field generating device to alternately produce active and substantially inactive electromagnetic field portions by selectively energizing the coil, each said active electromagnetic field portion having a frequency of between 1 Hz and 100 Hz and comprising a plurality of generally rectangularly-shaped electromagnetic field pulses wherein each electromagnetic field pulse has a duration of between 25 μs and 100 ms, each said substantially inactive electromagnetic field portion including no electromagnetic field pulses, wherein the duration of the inactive electromagnetic field portion is longer than the duration of the active electromagnetic field portion.

28. The apparatus of claim 27, wherein the control device comprises a microcontroller programmable by a user so that an electromagnetic signal pattern corresponding to a predetermined therapeutic substance delivery plan is produced.

29. The apparatus of claim 27, wherein the electromagnetic field pulses have an electromagnetic field strength of less than or equal to 3 Gauss and sufficient to facilitate transdermal delivery of therapeutic substances by increasing dermal permeability of a portion of the skin of a user of the apparatus.

* * * * *